United States Patent
Adam

(10) Patent No.: US 6,355,043 B1
(45) Date of Patent: Mar. 12, 2002

(54) BONE SCREW FOR ANCHORING A MARROW NAIL

(75) Inventor: Michael Adam, Cham (CH)

(73) Assignee: Sulzer Orthopedics Ltd., Baar (CH)

( * ) Notice: Subject to any disclaimer, the term of this patent is extended or adjusted under 35 U.S.C. 154(b) by 0 days.

(21) Appl. No.: 09/473,775

(22) Filed: Dec. 29, 1999

(30) Foreign Application Priority Data

Mar. 1, 1999 (EP) .............................................. 99810171

(51) Int. Cl.$^7$ ................................................ A61B 17/84
(52) U.S. Cl. ............................ 606/72; 606/62; 606/73
(58) Field of Search ................................. 711/413, 385, 711/411, 415; 606/60, 62, 64, 65, 67, 72, 73

(56) References Cited

U.S. PATENT DOCUMENTS

| 4,622,959 | A |   | 11/1986 | Marcus |         |
|-----------|---|---|---------|--------|---------|
| 5,217,462 | A | * | 6/1993  | Asnis et al. | 606/73 |
| 5,259,398 | A | * | 11/1993 | Vrespa | 128/898 |
| 5,536,127 | A |   | 7/1996  | Pennig |         |
| 5,593,410 | A | * | 1/1997  | Vrespa | 606/73 |
| 5,601,553 | A | * | 2/1997  | Trebing et al. | 606/61 |
| 5,653,710 | A | * | 8/1997  | Harle | 606/73 |
| 5,713,901 | A |   | 2/1998  | Tock |         |
| 5,743,914 | A | * | 4/1998  | Skiba | 606/73 |
| 5,925,048 | A | * | 7/1999  | Ahmad et al. | 606/73 |
| 5,935,127 | A | * | 8/1999  | Border | 606/62 |
| 5,954,722 | A | * | 9/1999  | Bono | 606/61 |
| 6,030,162 | A | * | 2/2000  | Huebner | 411/413 |
| 6,048,344 | A | * | 4/2000  | Schenk | 606/73 |
| 6,080,159 | A | * | 6/2000  | Vichard | 606/64 |
| 6,129,730 | A | * | 10/2000 | Bono et al. | 606/73 |

FOREIGN PATENT DOCUMENTS

| EP | 0 424 734 A1 | 5/1991 |
| EP | 0 865 769 A1 | 9/1998 |

* cited by examiner

Primary Examiner—Paul J. Hirsch
Assistant Examiner—Michael B. Priddy
(74) Attorney, Agent, or Firm—Townsend and Townsend and Crew LLP

(57) ABSTRACT

A Bone screw for anchoring a marrow nail with transverse bores in a tubular bone. The bone screw had a thread with a pitch S, a core diameter $D_1$ and outer diameter $D_3$. The screw supports the marrow nail with a middle part and is fixed in the bone with a distal part. The thread has a flat cylindrical thread base with a length l>0.3 S. In addition, a second thread with the same pitch S and with the core diameter $D_1$ is present in a proximal head part, but has a greater outer diameter $D_2>D_3$ in order to proximally achieve a fixing with a greater thread profile.

7 Claims, 2 Drawing Sheets

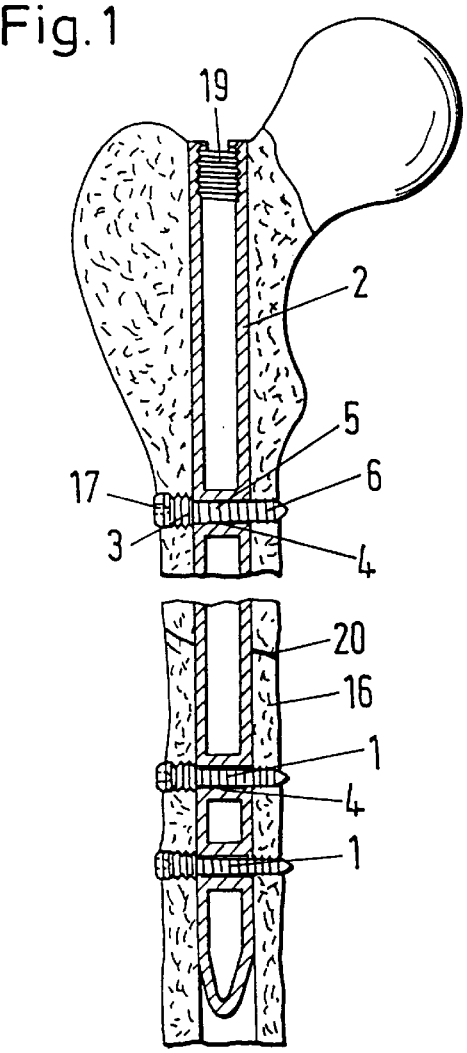
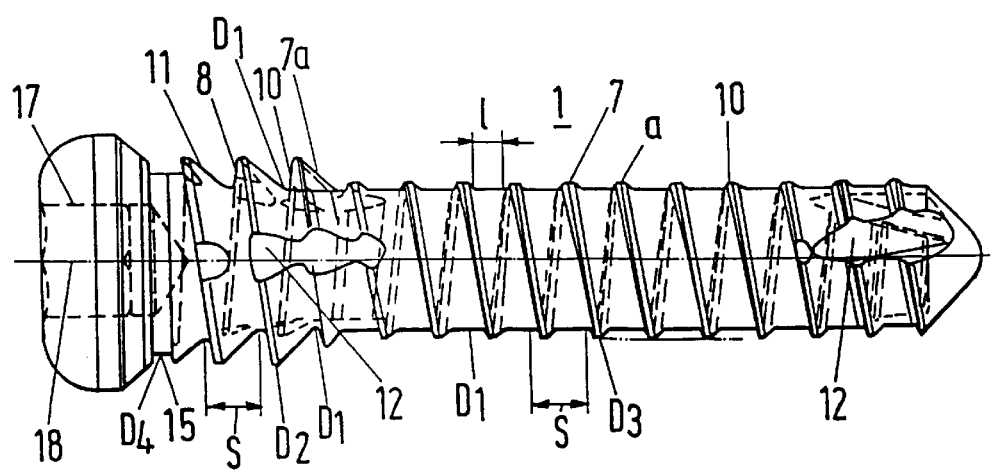

BONE SCREW FOR ANCHORING A MARROW NAIL

BACKGROUND OF THE INVENTION

1. Field of the Invention

The invention relates to a bone screw for anchoring a marrow nail.

2. Description of the Prior Art

Marrow nails are used for the support of fractures at tubular bones. As a rule marrow nails are hammered into the marrow chamber in order to provide the bone with an orientation in the longitudinal direction and subsequently to effect an additional anchoring of the marrow nail in the tubular bone with screw-like anchoring elements, which are passed through transverse bores in the marrow nail.

In U.S. Pat. No. 4,622,959 a marrow nail is shown which is connected to an aiming device at its proximal end after its hammering in into the femur bone, in order to pre-bore the tubular bone in alignment with its existng transverse bores and subsequently to turn in anchoring screws which are supported with their thread at both sides by the marrow nail.

Anchoring pins and screws for marrow nails are also shown in the layering open print DE-A-32 44 243 and in the German utility model G 89 0744 3.2. Common to the listed references is that the fixing of the bone screw in its proximal region takes place with the same outer diameter as is present in the lateral thread part. In this the fixing takes place in the relatively hard corticalis of the tubular bone. A through-going screw thread which is intended to support the marrow nail with its middle region has the disadvantage that the bone loses its stretch in the proximal region of the screw due to the large screw-in length. A cylindrical prolongation of the lateral screw thread with its outer diameter into the proximal region results in a rupture action in the bone which can be countered only through an approaching of the core diameter to the outer diameter of the thread. This means that in the lateral region of the screw the thread is in such a case limited in its shaping in the proximal region by the rupture action of the cylindrical part.

SUMMARY OF THE INVENTION

The object of the present invention is to improve the fixing of a securing screw. This is achieved with the thread having a flat cylindrical thread base with a length l>0.3 S and in that in the proximal head part a further thread part with the same core diameter $D_1$ and with similar thread with the same core diameter $D_1$ and with the same pitch S as in the distal part, however with a greater outer diameter $D_2>D_3$, is provided in order to achieve a good fixing proximally and distally.

An advantage of this arrangement consists in that the geometry of the two threads can be adapted to the low yielding tendency of the corticalis. Both threads travel a short distance with in each case their own thread profile during their common penetration into the corticalis.

With an outer diameter of the proximal thread which is greater than the inner diameter of the transverse bore in the marrow nail it is ensured that the proximal part forms its own thread in the bone. In addition the thread profile is formed asymmetrically, with an inclination towards the proximal which is greater than the inclination towards the distal in order to keep the specific pressure load small, which arises on the proximally directed flank for producing a forward thrust force. Inclinations of the projecting thread profile towards the distal between 40° and 50° and towards the proximal between 75° and 87° are provided.

Notches are laid through the thread profiles so that cutting edges arise which prevent excessive radial forces and a bursting of the bone during the screwing in.

Furthermore, it is advantageous to provide the thread tips of the thread profile with a flattening of $0.1\ \text{mm} \leq a \leq 0.8$ in the middle part and in the distal part in order that a sufficiently carrying surface is present between the transverse bore and the bone screw. A further improvement can be achieved when the proximally directed flanks at the reverse side lie on a common helix, because then a guided forward thrust movement is present independently of the momentary screw-in depth.

For the manufacture of the two thread parts with a common helix for the proximally directed flank and also in general for two different thread profiles, circular milling with two corresponding generators is useful. The profile milling tools with their axis are in each case pivoted relative to the screw axis and are guided around helically relative to the screw slug in order to mill the thread base.

Furthermore, it is advantageous to provide a puncture or a cut-out in the region proximal of the thread at the head part which prevents the core diameter of the thread from running out conically. Precisely at this location an undesirable rupture effect can arise, which produces tears in the bone.

BRIEF DESCRIPTION OF THE DRAWINGS

FIG. 1 schematically illustrates a longitudinal section through a femur bone with a marrow nail which is secured at transverse bores with bone screws;

FIG. 2 schematically illustrates an enlarged view of a suitable bone screw; and

DETAILED DESCRIPTION OF SPECIFIC EXEMPLARY EMBODIMENTS

Figure 3:
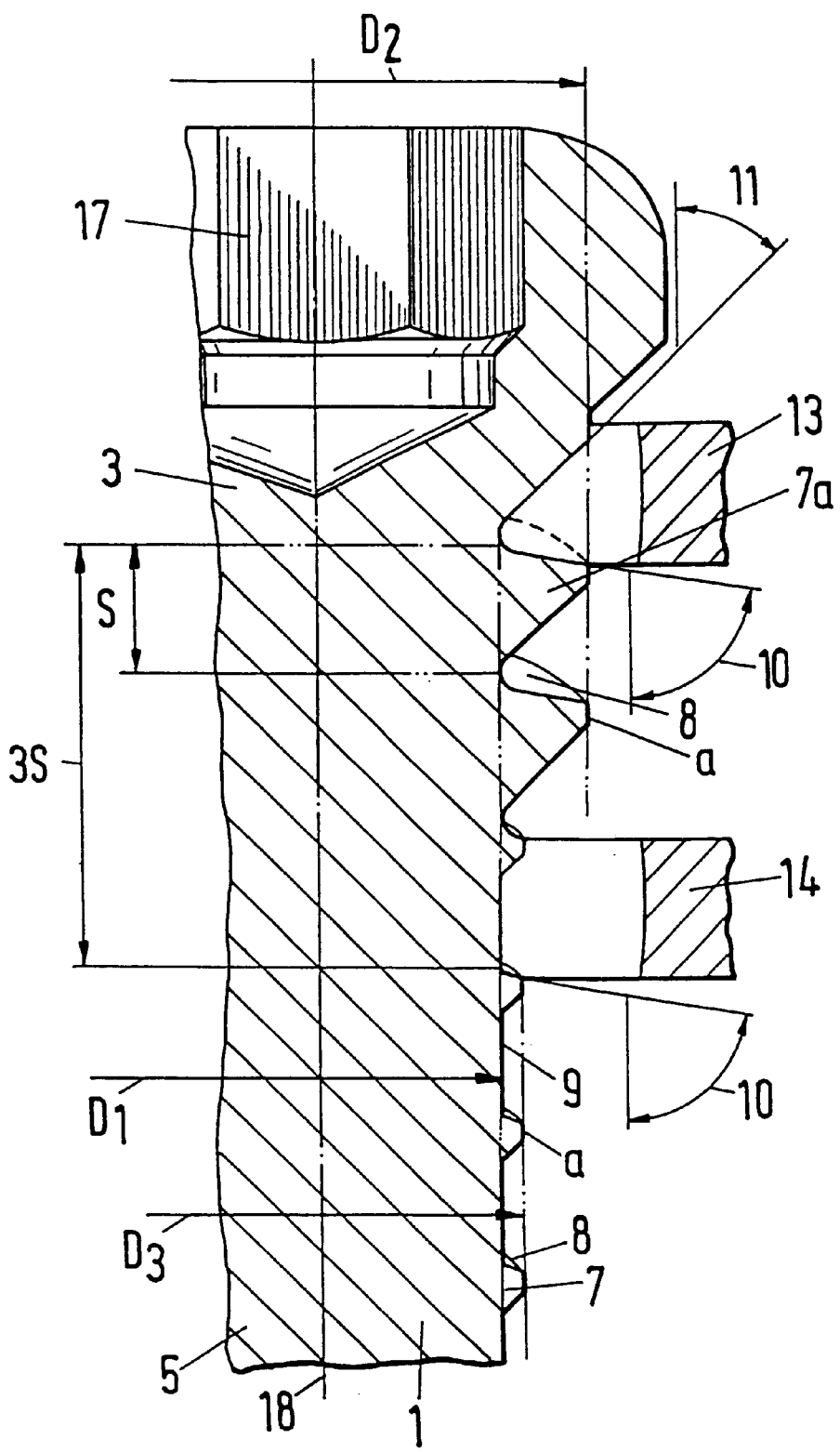
FIG. 3 schematically illustrates an enlarged view of a further bone screw, which can be manufactured through circular milling.

Bone screws 1 for anchoring a marrow nail 2 with transverse bores in a tubular bone are shown in the figures. The bone screws 1 have a thread 7 with a pitch S, with a core diameter $D_1$ and with outer diameter $D_3$, which supports the marrow nail with the middle part 5 of the screw and fixes the screw 1 in the bone with the distal part 6, with the thread having a flat cylindrical thread base 9 with a length l>0.3 S. In addition, a second thread 7a with the same pitch S and with the core diameter $D_1$ is present in the proximal head part 3, however with a greater outer diameter $D_2>D_3$ in order proximally to achieve a fixing with a greater thread profile.

In FIG. 1 a marrow nail 2 bridges over a fracture location 20 in a femur bone 16. At both sides of the fracture location 20 the marrow nail 2 has transverse bores 4 which guide bone screws 1, which themselves are fixed distally and proximally in the bone 16 with thread profiles 7, 7a of different sizes and of the same pitch S. With an aiming device (not shown here) which can be connected to the marrow nail 2 with a mounting 19, bores which are concentric to the transverse bores 4 are pre-bored into the bone 16 in order afterwards to turn in the bone screws 1 with the help of an inner hexagon 17 of the proximal head part 3.

A first bone screw 1 is shown in FIG. 2. Its head part 3 begins proximally with an actual screw head which has an inner hexagon 17 and a large thread profile 7a with core diameter D and outer diameter $D_2$ and with a pitch S, which is interrupted by notches 12. The reverse-side, proximally directed flank 8 of the thread profile 7a forms together with the axis 18 of the screw an inclination 10 of 83° and the distally directed flank an inclination 10 of 45°. The thread profile 7a ends towards the proximal in a groove 15, which separates the thread profile 7a from the actual screw head.

The inner diameter $D_4$ of the groove 15 is significantly less than the outer diameter $D_2$ of the thread 7a. A second thread 7, likewise with the pitch S and the core diameter $D_1$, is provided in the middle and the distal part of the screw 1. This thread 7 lies with its proximally directed flank on the same helix as the flank 8 of the thread profile 7a at the proximally directed head part. In contrast, the outer diameter $D_3$ of the second thread 7 is significantly smaller so that, while the inclinations 10, 11 are maintained, a smaller thread profile 7 with a cylindrically flat thread base of the length l>0.3 S arises. A variant embodiment provides for example for a pitch S=1.75 mm, a core diameter $D_1$=4.3 mm, an outer diameter $D_2$=6.5 mm in the proximal thread 7a and an outer diameter $D_3$=4.9 mm in the middle and distal thread part, whereas a flattening a=0.2 mm is provided for the thread tips. Notches are likewise provided in the distal part towards the screw tip which allow cutting edges to arise in order to prevent ring tensions in the bone which are too great.

In FIG. 3 a further example is shown with the same reference symbols as in FIG. 2. In addition profile milling tools 13, 14 are shown, which come into use one after the other in circular milling in order to produce the two threads 7a, 7 with a through-going helix of the proximally directed flank 8. After the screw slug 3 has been machined with its outer diameters $D_2$, $D_3$, a thread 7a is first milled in the proximal head part 3 with a profile milling tool 13. The profile milling tool 13, which is placed at an inclination corresponding to the pitch S, is first lowered radially to the screw axis 18 and then moved along a screw line with the pitch S on the screw 1 in order to mill the thread 7a of the head part 3. Then a second profile milling tool 14 is brought into engagement at a distance from the profile of the first milling tool 13 in order to mill the second thread 7, with the distance of the proximally directed flanks 8 corresponding to an integral multiple of the pitch S in the same longitudinal section.

What is claimed is:

1. A bone screw for anchoring a marrow nail, and penetrating the marrow nail transversely with a distal part in a suitable transverse bore and supporting the marrow nail with a middle part at the transverse bore, the screw comprising a head part for the application of a turning-in tool, the middle part and the distal part including a thread having a pitch S, and a core diameter $D_1$ and an outer diameter $D_3$, wherein the thread includes a cylindrical core part having a length l>0.3 S; wherein a proximal portion of the head part includes a proximal thread with the same core diameter $D_1$ and with the same pitch S as the thread distal part, but having an outer diameter $D_2$ that is greater than the outer diameter $D_3$ of the distal part and that is greater than the inner diameter of the transverse bore in the marrow nail; and wherein a reverse-side, proximally directed flank of both threads is on a common helix.

2. A bone screw in accordance with claim 1 wherein a proximally projecting thread profile of the screw is provided that is designed asymmetrically with an inclination towards the proximal portion which is greater than the inclination towards the distal part.

3. A bone screw in accordance with claim 1 wherein the screw has an inclination of a projecting thread profile that amounts to between 40° and 50° towards the distal part and between 75° and 87° towards the proximal portion.

4. A bone screw in accordance with claim 1 further comprising notches that are laid through thread profiles that enable a cutting of the thread profile during screwing in of the screw.

5. A bone screw in accordance with claim 1 wherein thread tips of the thread profile in the middle part and in the distal part have a flattening of 0.1 mm≦a≦0.8 mm.

6. A bone screw in accordance with claim 1 further comprising, in a region proximal of the thread at the head part, a cut-out with a diameter $D_4<D_2$ in order to prevent an impermissible increase of the core diameter during the screwing in.

7. Method for the manufacture of a bone screw for anchoring a marrow nail, and penetrating the marrow nail transversely with a distal part in a suitable transverse bore and supporting the marrow nail with a middle part at the transverse bore, the screw comprising a head part for the application of a turning-in tool, the middle part and the distal part including a thread having a pitch S and a core diameter $D_1$ and an outer diameter $D_3$, wherein the thread includes a cylindrical core part having a length l>0.3 S, wherein a proximal portion of the head part includes a proximal thread with the same core diameter $D_1$ and with the same pitch S as the thread distal part, but having an outer diameter $D_2$ that is greater than the outer diameter $D_3$ of the distal and that is greater than the inner diameter of the transverse bore in the marrow nail, and wherein a reverse-side, proximally directed flank of both threads is on a common helix; and wherein the thread profiles of the head part and of the middle part and the distal part are produced through circular milling with profile milling tools in order to produce two different thread profiles with the same pitch S.

* * * * *